(12) United States Patent
Stonisch

(10) Patent No.: US 7,520,747 B2
(45) Date of Patent: Apr. 21, 2009

(54) DENTAL TEMPLATE AND METHOD OF VISUALLY DEMONSTRATING AN OVERLAY FOR A DENTAL PATIENT AND SETTING THE HORIZONTAL PLANE WITH AN OVERLAY

(76) Inventor: Mary Sue Stonisch, 1690 Faircourt, Grosse Pointe Woods, MI (US) 48236

( * ) Notice: Subject to any disclaimer, the term of this patent is extended or adjusted under 35 U.S.C. 154(b) by 393 days.

(21) Appl. No.: 11/226,113

(22) Filed: Sep. 14, 2005

(65) Prior Publication Data
US 2007/0009855 A1  Jan. 11, 2007

Related U.S. Application Data

(63) Continuation-in-part of application No. 11/096,602, filed on Apr. 1, 2005, now abandoned.

(51) Int. Cl.
*A61C 5/00* (2006.01)
(52) U.S. Cl. .................. 433/215; 433/167; 433/196
(58) Field of Classification Search ................ 433/229, 433/219, 218, 215, 167, 196
See application file for complete search history.

(56) References Cited

U.S. PATENT DOCUMENTS

| | | |
|---|---|---|
| 1,654,387 A | 12/1927 | Stenz |
| 2,169,719 A | 8/1939 | Bush |
| 2,789,353 A | 4/1957 | Biggs |
| 4,247,287 A | 1/1981 | Gigante |
| 4,583,947 A | 4/1986 | Hazar |
| 4,710,127 A | 12/1987 | Bellavia et al. |
| 4,906,186 A | 3/1990 | France |
| 5,378,737 A | 1/1995 | Jacobs et al. |
| 5,639,235 A | 6/1997 | Lapointe et al. |
| 5,894,017 A | 4/1999 | Sagel et al. |
| 5,904,481 A | 5/1999 | Shima |
| 5,916,653 A | 6/1999 | Kunstadter et al. |
| 5,951,291 A | 9/1999 | Albert et al. |
| 6,063,830 A | 5/2000 | Deguchi et al. |
| 6,398,550 B1 | 6/2002 | Cartitg |
| 6,422,864 B1 | 7/2002 | Glatt |
| 6,820,623 B2 | 11/2004 | Cook |

(Continued)

OTHER PUBLICATIONS

Website Literature, Fake Teeth Sytles in Hardwear, website—www.drbukk.com/bukkstyles.html., 7 pages, printed from website Dec. 10, 2004.

*Primary Examiner*—Ralph A Lewis
(74) *Attorney, Agent, or Firm*—Reising Ethington P.C.

(57) ABSTRACT

A dental prosthesis or template (10) simulates the front surfaces of a patient's teeth and is overlayed over a patient's natural teeth (40) to provide an indication of what a dental porcelain overlay may look like once applied to the patient's teeth. The dental template preferably is made from a flexible urethane or sanaprene material to allow the template to be applied against the person's natural teeth and temporarily adhere the template to his teeth provide for the visual demonstration of potential improvement to the patient's smile. The dental template (10) can be adhered to a set gel or registration paste to set the facial plane (75) at which the overlay should lie relative to the tooth plane (73) of the natural teeth (40) to establish a final restoration with an ideal and naturally appearing aesthetic result as it relates to horizontal facial planes and facial appearances.

4 Claims, 5 Drawing Sheets

U.S. PATENT DOCUMENTS

| | | | |
|---|---|---|---|
| 7,118,375 B2 * | 10/2006 | Durbin et al. | 433/68 |
| 7,153,131 B2 | 12/2006 | Crohn | |
| 7,175,427 B2 * | 2/2007 | Smith | 433/9 |
| 2004/0166463 A1 | 8/2004 | Wen et al. | |
| 2004/0229185 A1 | 11/2004 | Knopp | |
| 2005/0014109 A1 | 1/2005 | Lim | |
| 2005/0042569 A1 | 2/2005 | Phan et al. | |
| 2005/0196728 A1 | 9/2005 | Goldiner | |
| 2007/0009855 A1 * | 1/2007 | Stonisch | 433/215 |
| 2007/0059667 A1 * | 3/2007 | Lim | 433/219 |

* cited by examiner

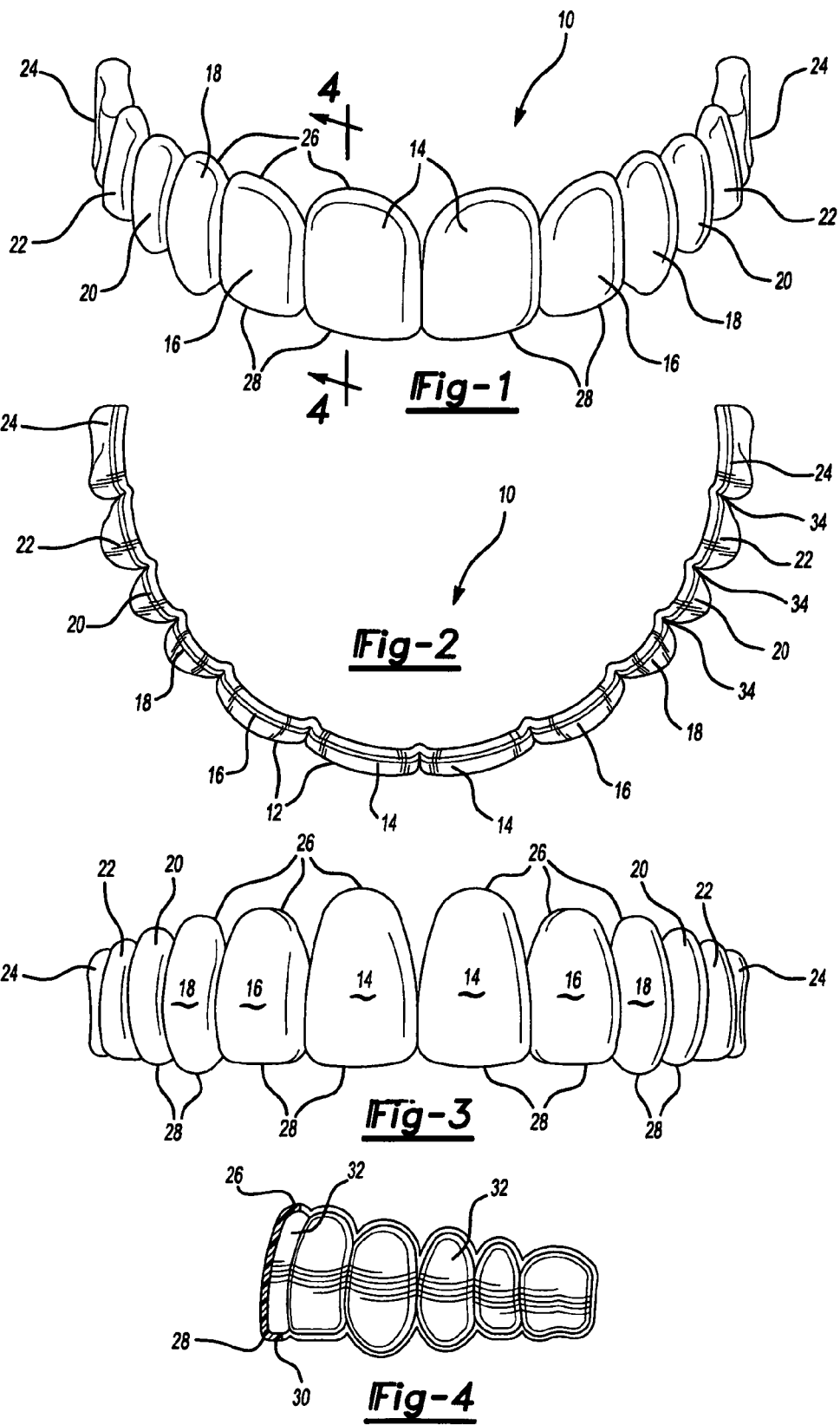

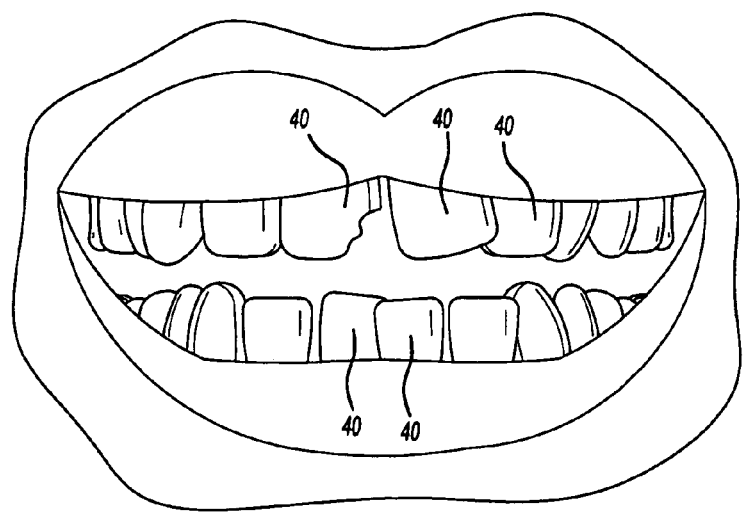
Fig-5
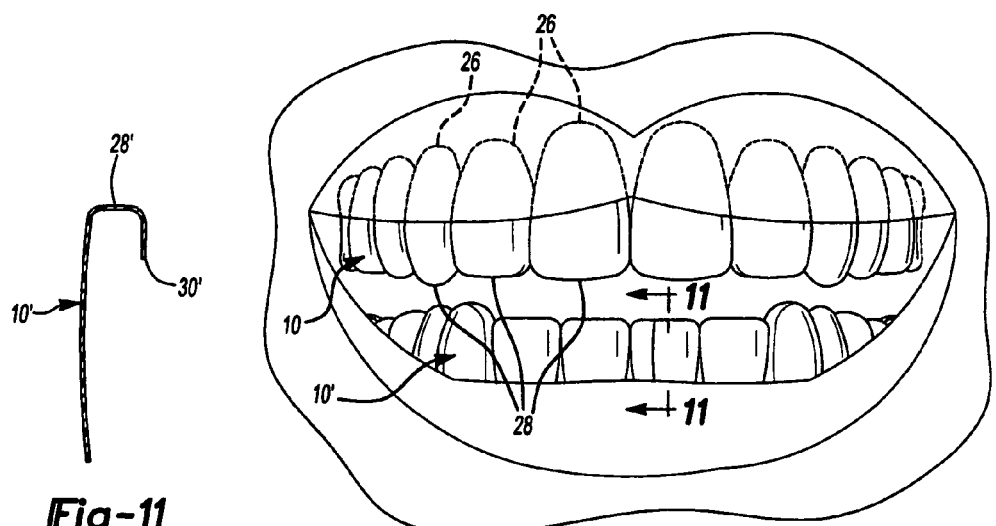
Fig-11
Fig-6
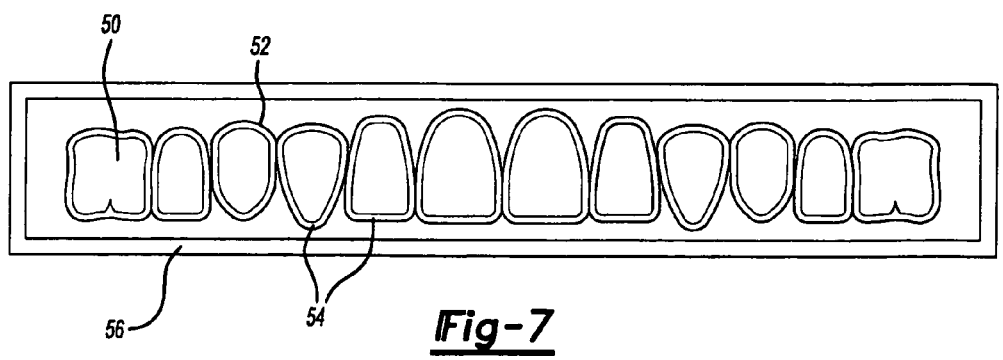
Fig-7

DENTAL TEMPLATE AND METHOD OF VISUALLY DEMONSTRATING AN OVERLAY FOR A DENTAL PATIENT AND SETTING THE HORIZONTAL PLANE WITH AN OVERLAY

This application is a continuation-in-part of U.S. Ser. No. 11/096,602 filed on Apr. 1, 2005, now abandoned.

TECHNICAL FIELD

The field of this invention relates to demonstration dental templates and a method for providing a visual representation to a dental patient of a potential overlay.

BACKGROUND OF THE DISCLOSURE

Human beings are a social animal and a person's face communicates important information to other people. A smile is a very important part of human communication and socialization. A genuine broad smile can help a person fit in and makes others who see the smile comfortable and even happy by seeing someone else's smile.

Teeth are an important part of a person's smile. Unattractive teeth or defects in a person's teeth can detract from the overall appearance of the smile. Dentists have long improved defective teeth with a porcelain overlay to enlarge, straighten, brighten, or fill in breaks or gaps in a person's teeth. A person who has excessively small teeth in part to excessive gums can enlarge the teeth by recontouring the gum line with the removal of some gum tissue in conjunction with a new overlay. People with yellow teeth or dark stains in their teeth can brighten their smile with a brighter whiter porcelain overlay.

As important as a smile is, many people with serious and unsightly defects in their smile decline to have a porcelain overlay to improve the smile for various reasons. One of these reasons is that a person may not be willing to undergo a permanent and irreversible operation unless there is a high assurance in the person's mind that the procedure will greatly enhance one's smile and the overlay will be comfortable in the mouth against one's natural teeth. The person may not have the vision or knowledge as to how such an overlay can improve one's smile. A person may initially resist the incorporation of dental prosthesis by being under the impression that the prosthesis may be uncomfortable in the mouth. Dentists until now had no easy method to demonstrate how such an overlay can improve the smile or to counteract the fears of discomfort. As such, only a limited amount of potential consumers accept and undergo an overlay procedure even though this dental treatment could greatly benefit a vastly wider consumer group.

A patient may not be willing to undergo a permanent dental procedure such as an overlay until he/she is fully assured with the knowledge that the procedure is right for him/her and will produce some dramatic and known result. The patient needs to see the image of his/her own face and smile in a dynamic setting in a more three dimensional demonstration in order to obtain the needed assurance to undergo the permanent porcelain overlay.

Recently, efforts have been made to visually demonstrate to the patient how a porcelain overlay may improve one's smile. One such attempt is to take a photograph of a person smiling and then digitally alter the teeth to produce the desired smile improvement. While the digitization can produce a number of different looks by digitally altering the teeth in a variety of ways, this process is less than optimal. The result produces a somewhat static and two dimensional look to the patient. It also gives no knowledge to the consumer related to the comfort of a porcelain overlay in the mouth.

Attempts have been made to place a temporary molded overlay of an individual tooth on a person's tooth. The overlay may adhere to the natural tooth for a short period of time in order to demonstrate to others the benefits and potential outcome of enhancing one's teeth for a better smile. The temporary molded overlay is made from a hardenable putty or resin shaped and cured onto a patient's particular tooth. While this method can provide the dynamic and three dimensional demonstration needed for the potential dental patient, it is a time consuming a costly procedure for fitting a plurality of teeth.

Once a patient decides to undergo cosmetic dentistry and obtain a porcelain overlay, the patient's teeth are prepared to receive the overlay. The overlay is then made using a mold impression of the prepared teeth. The mold contains the impression of the teeth along the tooth plane, however, the mold often does not provide adequate information as to the horizontal inclinations and facial planes with respect to the tooth plane. Often, the appearance of the overlay teeth need to be aligned with a facial plane that is angled with respect to the plane of the natural teeth for the best appearance. Dentists have in the past approximated the best angle by placing a stick, such as a cotton swab, into the registration paste before it has set to indicate the horizontal plane of the overlay with respect to the tooth plane. This placement was done with no visual representation of human teeth and as such could only provide approximation to the ideal position.

What is needed is a pre-fabricated demonstration dental template that can quickly be adhered to patients' teeth to demonstrate the look of a dental overlay for the patient. What is also needed is a dental prosthesis in the form of a dental template that provides the visual and tactile indicator to allow the consumer or patient to make a better educated decision prior to the onset of an aesthetic dental treatment; namely the application of a porcelain overlay. What is also needed is a method of visually demonstrating how a dental prosthesis can improve one's smile. Further, what is needed is a method to use the demonstration template also as a visual indicator to assist in determining the desired horizontal facial plane for the overlay relative to the natural tooth plane and be set in a mold to maintain and be able to communicate information of the desired horizontal facial plane for the overlay relative to the natural teeth with the laboratory to facilitate ideal end results with respect to facial planes and symmetry.

SUMMARY OF THE DISCLOSURE

In accordance with one aspect of the invention, a demonstration dental template is in the form of a unitary substrate curved to conform to the extrados of the arch of a patient's natural teeth the dental template includes a rear surface shaped to abut against an outer side of patient's lower or upper teeth and to overlay on the patient's teeth. The template has a front exposed surface having visual representation of a plurality of real teeth. The proximate cervical edge often referred to as the cervical edge of the template defines the gum line with the teeth and a distal edge often referred to as an incisal (biting) edge defines the ends of the teeth.

The rear surface preferably has an adhesive thereon for temporarily adhering the template to the teeth of the patient. The adhesive strength should be weak enough allow the dentist to easily pull the template off of the natural teeth. The adhesive may be a coating pre-applied to the template or applied in situ by the dentist.

In one embodiment, the substrate is an elastomeric material with a glazed three dimensional front surface simulating a porcelain surface to mimic the size, shape and texture of natural teeth. It is desirable that the incisal (biting) edge has a flange for extending about the natural tooth end. The substrate is flexible to allow the template to conform about any protruding teeth and to fit differently sized extradoses of the arches of the patent's natural teeth. In one embodiment, the pre-fabricated template is a dental template shaped to mimic at least the central incisors, lateral incisors, cuspids and first pre-molars, of the upper teeth. The template can be cut to remove any unneeded teeth such as for example second pre-molars, and first molars if they are initially part of the template.

In another embodiment, the demonstration dental template may be formed by a flat strip with a cervical edge having the shape of teeth at the gum line and the opposing incisal edge having the contour of incisal ends of the teeth crowns. The front side has shading to simulate individual teeth.

In this embodiment, the strip may have its front side simulating the central incisors, lateral incisors, cuspids, first pre-molars, second pre-molars and first molars and may be cut to remove unneeded teeth for a demonstration. The strip may be pre-cut and peelable from a protective backing. The strip may have a pre-applied adhesive backing that is protected by the protective backing.

In accordance with another aspect of the invention, a method visually demonstrating an improved smile to a dental patient includes the steps of temporarily placing a demonstration dental template to overlay in front of the teeth, preferably the upper teeth, of a patient, temporarily adhering the dental template to the natural teeth to allow removal of the dentist's or technician's hand to provide an unobstructed view of the demonstration template to the patient via a mirror, camera or other visual aid and removing the demonstration dental template from the natural teeth. The dental template extends from the gum line to the incisal (biting) edge of the natural teeth and shaped and surfaced to mimic the look of natural teeth.

The method preferably also includes placing the demonstration dental template over the central incisors, lateral incisors, cuspids and first pre-molars of the patient's upper teeth.

The method also preferably includes having a demonstration dental template being shaped to mimic and cover the central incisors, lateral incisors, cuspids, first pre-molars, second pre-molars and first molars and cutting off distal ends of the template if not needed for a patient's demonstration.

In accordance with another aspect of the invention, a method for setting the horizontal plane of a dental prosthesis overlay includes preparing natural teeth for the installation of a porcelain overlay; applying a setting material, for example a gel or paste generally referred to as a paste, to envelope the natural teeth to form a series of mold cavities lying in a tooth plane. A dental template is positioned on the paste at a desired horizontal facial plane such that the template appears horizontal relative to the horizontal facial plane for example with the top of head, forehead, eyebrows, eyes or cheekbones.

The paste is set with the dental template in a set position to match the desired horizontal position of the final porcelains or other prosthesis. The paste and template are then removed as an assembled unit from the natural teeth such that the paste mold cavities correspond in negative shape to the prepared natural teeth forming along the tooth plane and the dental template maintains its set position to record the position of the horizontal facial plane of the template relative to the tooth plane of the natural teeth. The assembled unit can be sent to the laboratory and used on the master model of prepared teeth to communicate desired horizontal of the overlay.

Preferably, a rear surface of the dental template is positioned onto the setting paste before the paste becomes set and the front surface of the template retains its visibility in front of the paste. It is desirable to align a plurality of individual upper teeth representation of the template in front of the individual natural teeth.

In accordance with one embodiment of the invention, a method for visually demonstrating an improved smile to a dental patient and setting the horizontal facial plane of a dental overlay includes temporarily placing a demonstration dental template to overlay in front of the teeth of a patient, temporarily adhering the dental template to the teeth to allow removal of the dentist's or auxiliary's hand to provide an unobstructed view of the demonstration template to the patient via a mirror, camera or other visual aid with the dental template extending from the gum line to the incisal crown ends of the teeth and shaped and surfaced to mimic the look of natural teeth. The demonstration dental template is then removed from the natural teeth, and natural teeth are prepared for the installation of a porcelain overlay. A setting paste is applied to envelope the natural teeth to form a series of mold cavities lying in a tooth plane of the natural teeth. The demonstration dental template is then positioned on the gel at a desired horizontal facial plane such that the template appears horizontal relative to the horizontal facial plane as previously mentioned. The paste is set with the demonstration dental template in a set position. The set paste and demonstration dental template are then removed as an assembled unit from the natural prepared teeth such that the paste mold cavities correspond in negative shape to the prepared natural teeth forming along the tooth plane and with the demonstration dental template maintains its set position to record the position of the facial plane of the template relative to the tooth plane of the natural teeth.

In accordance with another aspect of the invention, a mold for use in manufacturing a dental overlay includes a rear section having cavities corresponding in shape with natural teeth to be overlaid. The cavities lay along a first tooth plane corresponding to a tooth plane of the natural teeth. A front dental template section visually representing a plurality of individual teeth mounted at the front section of the paste mold with the front dental template aligned along a facial plane which may be canted with respect to the first tooth plane.

Preferably the mold has its rear section that has the cavities made from a setting paste and the front dental template section made from a plastic material. The front dental plastic material is affixed to the setting paste as it sets.

BRIEF DESCRIPTION OF THE DRAWINGS

Reference now is made to the accompanying drawings in which:

FIG. 1 is a perspective view of a dental template in accordance with one embodiment of the invention;

FIG. 2 is a top plan view of the dental template as shown in FIG. 1;

FIG. 3 is front elevational view of the dental template as shown in FIG. 1;

FIG. 4 is a cross-sectional view taken along lines 4—4 shown in FIG. 1;

FIG. 5 is a front view of a patient's smile before use of the dental template;

FIG. 6 is a front view demonstrating use of the dental template on a patient;

FIG. 7 is the front elevational view of an alternative embodiment disclosing the invention;

FIG. 11 is a cross sectional view of the lower template taken along FIG. 11-11 shown in FIG. 6;

DETAILED DESCRIPTION OF THE PREFERRED EMBODIMENT

Figure 8:
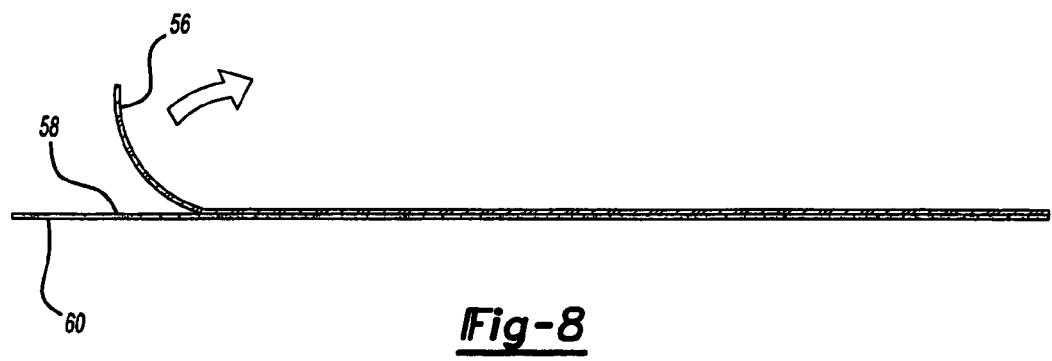
FIG. 8 is a top plan view of the embodiment shown in FIG. 7 showing the teeth peeled from its protective backing.
Figure 9:
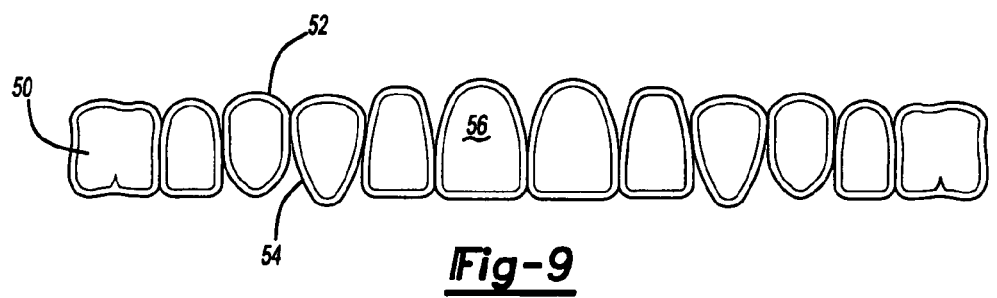
FIG. 9 is a elevational view of the embodiment shown in FIG. 7 with the front teeth removed from the backing.

Referring now to FIG. 1, a dental template 10 is shown that simulates natural teeth of a patient. Dental template 10 is made from urethane or sanaprene material and is shaped to be positioned to abut against the front surface of a patient's natural teeth 40 shown in FIG. 5. Front surface 12 of the template has a finished porcelain look to simulate natural teeth. The front surface 12 is scalloped to mimic the natural division of individual teeth such as the front central incisors 14, lateral incisors 16, cuspids 18, first premolars 20, second premolars 22 and first molars 24.

Top edge 26 of the dental template 10 is contoured to simulate the top of natural teeth to define the gum line. The incisal bottom edge 28 of the dental template simulate the incisal (or biting) end of the upper teeth. The biting (incisal) edge 28 as shown more clearly in FIGS. 3 and 4 forms a lip or ledge 30 to rest on the existing biting edge. The rear surface 32 is contoured with a generally flat-to-slightly concave negative shape to abut the individual natural teeth of the patient.

The urethane or sanaprene material allows the template to flex to match the extrados of the arch of the patient's natural teeth 40 and to abut against the patient's natural teeth 40. Other suitable flexible plastics or elastomeric materials with similar sanitary and flexible qualities can also be utilized in place of the urethane or sanaprene. A temporary adhesive or glue commonly referred to as a bite registration paste can be placed on the back surface 32 to retain the dental template in position against the patient's teeth 40 during inspection or examination. The adhesive may be pre-applied onto the template or may be applied in situ by the dentist or auxiliary personnel.

The dental patient or prospective dental patient can visually inspect the appearance of this dental template 10 in his mouth via a mirror. And can view the template from a variety of angles. In addition to the three dimensional visual aspect of the dental template the demonstration can provide indication of how a permanent porcelain will feel against the front surface of his natural teeth and lips during different smiles, biting and lip motions. As shown in FIGS. 5 and 6 the patient and prospective patient can quickly see the difference between his natural teeth 40 and natural smile with a smile that includes a porcelain overlay by looking at template 10 in position.

The method of demonstrating and improved smile to the patient becomes expeditious and time efficient. Providers such as a dentist, dental hygienist or other auxiliary personnel can merely place the dental template against the natural teeth of the patient. The dental template may extend over the gum line 26 to the incisal edge (biting edge) end 28 of the crown at the lower edge above the patient's natural teeth with the flange 30 wrapped around or ending beyond the edge of the patient's natural teeth. The template can be temporarily adhered to the teeth to allow the patient and prospective patient to inspect them dynamically in position. The patent can smile in a variety of ways and even talk while the template is in position. After inspection is over, the dental template is merely removed from the patient's or prospective patient's mouth and his teeth. As an option, because of the ease of insertion and removal of the template, the patient can leave the office with the template to insert at home to show a spouse or loved one for reassurance and decision making. This allows the consumer and potential patient to make a better educated decision prior to the commencement of aesthetic dental procedures, namely the application of dental porcelains.

The template can be manually maneuvered and placed in position by the dentist, technician or lay person. A mere grasping with a forefinger and thumb is often all that is needed to successfully place the template in position. Another installation device besides a hand is also foreseen to be used with this template.

In some instances, the first molars, second premolars, and first premolars and possibly the cuspids may not be needed to improve patient's smile. In these cases, the dental template is cut at one of the defined interstrices 34. In other words, there may be instances, wear the demonstration dental template has only the central incisors, lateral incisors, cuspids and first premolars. The rearward posterior teeth, i.e. the second premolars and first molars may be cut off the template 10 and discard.

The removal of the template is also quick and easy. The temporary adhesive should be of a known type that provides a relatively weak securement so that a manual pull on the template will remove it from the natural teeth. The adhesive may be of the same type that secures temporary crowns or inlays in place or be such that is used as a bite registration material.

Figure 10:
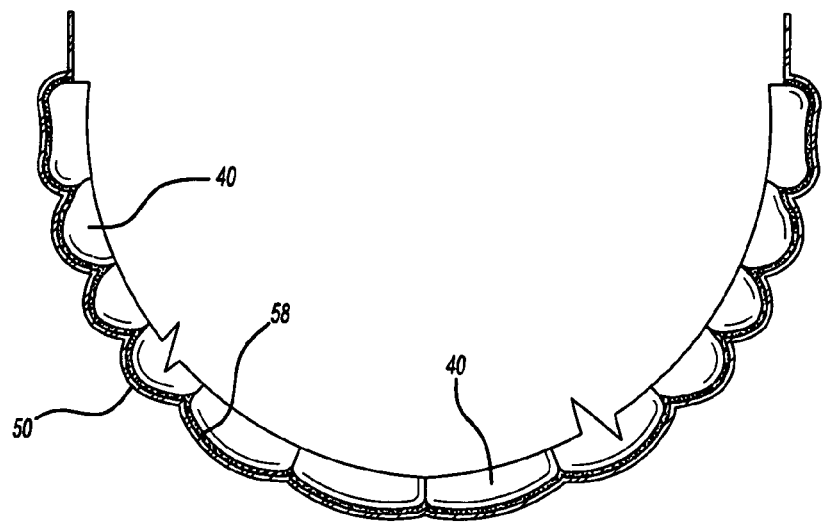
FIG. 10 is a top plan view of the alternative embodiment showing the strip in position against the natural teeth of a patient.

Another embodiment is shown in FIGS. 7-10. In the second embodiment, the dental template comprises a flat strip 50 that has contoured top and bottom edges 52 and 54. And the front surface 56 is photographed or shaded to simulate individual teeth and an adhesive backing 58 to adhere to the front teeth of the patient. The strip can be packaged flat and be peelable from a protective backing 60 that allows the adhesive backing to be easily peeled from the rear surface 58. The strip 50 is flexible to fit about the extrados of the arch of the natural teeth 40 and follow the contour of each individual tooth 40 as shown in FIG. 10.

The dental templates may be prefabricated in various sizes, styles and shades to better fit and cosmetically blend with different sized mouths and varying types and shades of teeth. The use of the dental template on the front upper teeth may quickly give a visual and tactile indicator to allow the consumer and potential patient to make a better education decision prior to the commencement of an aesthetic dental treatment namely the application of a dental overlay.

Templates 10' are also foreseen to be used on occasion with lower teeth as shown in FIG. 6. If the template 10' is made for lower teeth, care needs to be directed to make the template 10' thin enough as with the permanent porcelain overlay so as not to interfere with the patient's bite. The lower dental template 10' would also have its incisal end 28' wrap further over the incisal end of the lower teeth to keep the edge 30' of the template hidden from normal viewing angles of the lower arch.

The temporary installation of the template is simple enough that any of the above described embodiments can also be disseminated to potential patients as a mail piece for installation by a lay person in order to intrigue the prospective patient. The use of the three dimensional or flat sticker embodiments may be used by dentists or dental laboratories to heighten consumer awareness and to instigate a prospective patient to make an appointment for a consultation to further investigate the feasibility of specific smile enhancement options through cosmetic surgery.

Figure 12:
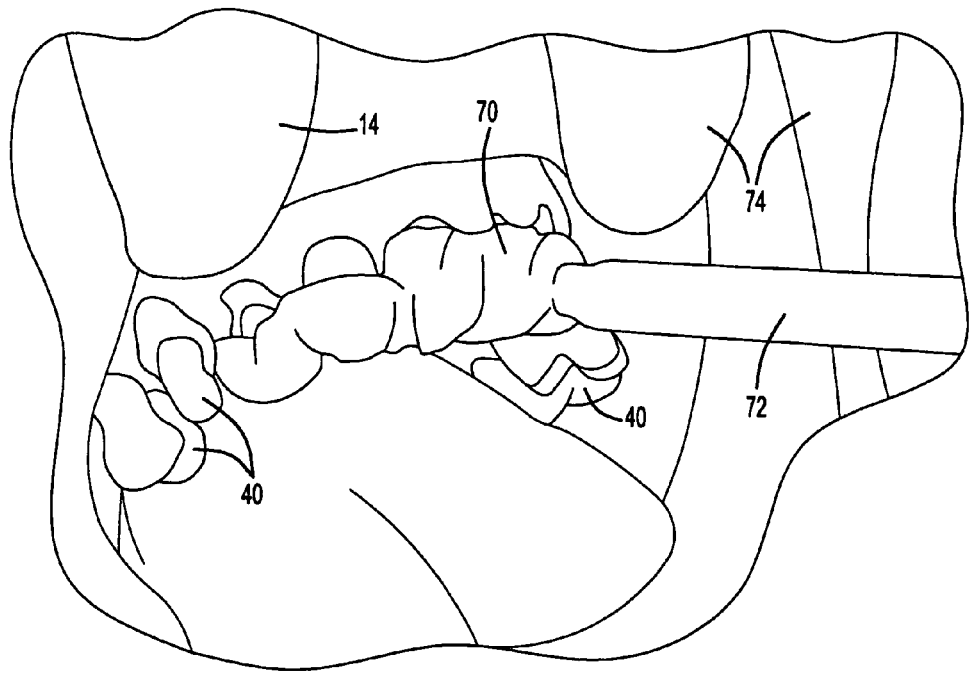
FIG. 12 is a view of paste being set onto prepared natural teeth.

The dental template can also be subsequently used to set the horizontal plane of the overlay when a patient decides to proceed with the cosmetic overlay. The patient has the natural teeth shaped and prepared to receive an overlay. After the natural teeth are properly shaped, a setting gel or bite registration paste 70 is placed to completely surround the prepared natural teeth 40 as shown in FIG. 12 such that an impression of the teeth 40 is made in the paste. The paste is delivered by a conventional applicator 72. The paste may be any of a variety of commercially available bit registration pastes. Blue Mousse by Parkell and Memosil 2 by Heraeus-Kulzer GmbYH and Co. KG are two suitable pastes. Other gels and pastes are also foreseen to be suitable.

Figure 13:
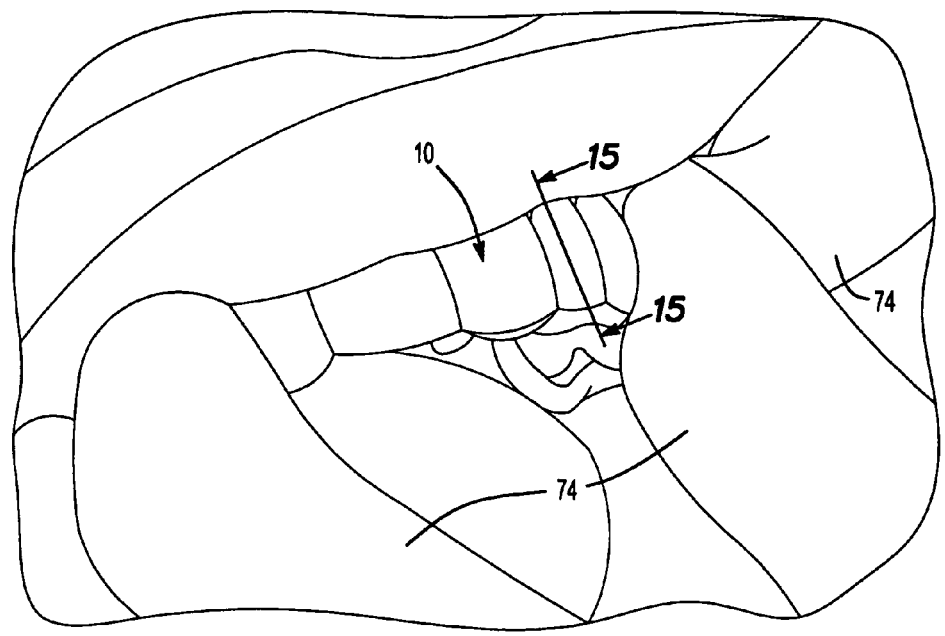
FIG. 13 is a perspective view of a dentist or auxiliary personnel applying the demonstration dental template positioned onto and affixed to the paste.
Figure 14:
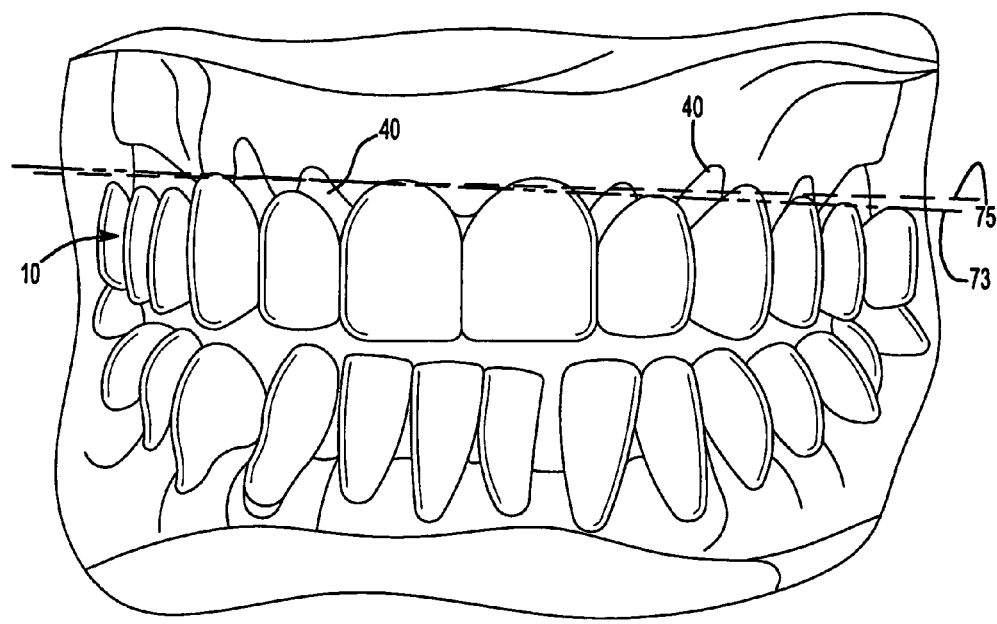
FIG. 14 is a partially schematic view illustrating a situation where the dental template is aligned with a horizontal facial plane and is canted with respect to the natural tooth plane.
Figure 15:
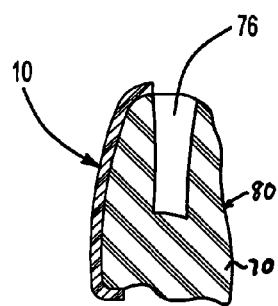
FIG. 15 is a cross-sectional view taken along lines 15-15 in FIG. 13 illustrating the mold formed from the set paste and the front dental template.

While the paste is setting, the dental template 10 is then placed on the paste as shown in FIG. 13. The template 10 floats on the registration paste 70 and can be manually moved by the dentist or auxiliary personnel by pressure from his fingers 74. As illustrated in FIG. 14, the template 10 may be horizontally positioned at an angle 75 compared to the natural tooth plane indicated as 73. The template angle 75 may be set at an angle that provides the best appearance for the overlay. The best horizontal facial plane may be visually determined by taking into account many horizontal planes of the face, i.e. the top of the head, the forehead, the eyebrow plane, the plane of the eyes, the plane of the cheek bones and the upper and lower lip angles and lower jaw.

Once the dentist sets the plane and confers with the patient that the template 10 is at the best horizontal facial plane, the paste 70 is then allowed to set with the template 10 in the set angle as shown in FIG. 14. Once the paste is set, the template is now securely affixed in place to the paste and the mold assembly 80 can be removed from the teeth 40 by gently pulling it away from the teeth. The mold 80 formed by the template 10 and the registration paste 70 can be shipped off to the lab for manufacturing the overlay. The paste 70 has a set of shaped cavities 76 that individually correspond to the natural teeth 40 and in series lie in the tooth plane 73. The template is affixed at the desired facial angle 75 independent from tooth plane 73. This desired facial angle can then be transferred to the working model to demonstrate to the laboratory technician the desired cant at which the porcelains or other restorations should be manufactured.

In this fashion, all information as to the tooth plane and facial plane are easily communicated to the technician of the overlay with a dental template. The dental template 10 has multiple purposes. Firstly to demonstrate the appearance of an overlay. Secondly, it helps visually to determine the appropriate facial plane in which the overlay should follow. Thirdly, the prepared mold communicates to the lab the appropriate facial angle of the overlay relative to the tooth plane to establish a horizontal tooth plane with ultimately ideal aesthetic results.

Other variations and modifications are possible without departing from the scope and spirit of the present invention as defined by the appended claims.

The embodiments in which an exclusive property or privilege is claimed are defined as follows:

1. A method visually demonstrating an improved smile to a dental patient and setting the horizontal plane of a dental overlay; said method comprising:
   temporarily placing a demonstration dental template to overlay in front of the upper teeth of a patient;
   temporarily adhering said dental template to said teeth to allow removal of any installation device to provide an unobstructed view of the demonstration template to said patient with said dental template extending from the gum line to the incisal crown ends of said teeth and shaped and surfaced to mimic the look of natural teeth and having a proximate edge shaped to mimic the shape of the cervical margin of said teeth at said gum line;
   removing said demonstration dental template from said teeth;
   preparing natural teeth for installation of a porcelain overlay;
   applying a registration paste to envelope said natural teeth with said paste following the contour of a tooth plane of said natural teeth positioning said demonstration dental template on said registration paste to align a tooth plane on said template with a desired horizontal facial plane such that said template appears horizontal relative to the horizontal facial plane;
   setting said paste with said demonstration dental template in a set position; and
   removing said paste and demonstration dental template as an assembled unit from said natural teeth such that said paste has cavities corresponding in negative shape to said natural teeth forming along said tooth plane and with said demonstration dental template maintaining the set position to record the position of the facial plane of the template relative to the tooth plane of said natural teeth.

2. A method as defined in claim 1 further comprising:
   positioning a rear surface of said demonstration dental template onto said setting gel before said paste becomes set; and
   retaining the front surface of said template visible in front of said paste.

3. A method as defined in claim 2 further comprising:
   aligning a plurality of individual upper teeth representations of said template in front of said individual natural teeth.

4. A method visually demonstrating an improved smile to a dental patient and setting the horizontal plane of a dental overlay; said method comprising:
   temporarily placing a demonstration dental template to overlay in front of the upper teeth of a patient;
   temporarily adhering said dental template to said teeth to allow removal of any installation device to provide an unobstructed view of the demonstration template to said patient with said dental template extending from the gum line to the incisal crown ends of said teeth and shaped and surfaced to mimic the look of natural teeth and having a proximate edge shaped to mimic the cervical margin of said teeth;
   removing said demonstration dental template from said teeth;
   preparing natural teeth for the installation of a porcelain overlay;

applying a registration paste to envelope said natural teeth with said paste following the contour of a tooth plane of said natural teeth positioning said demonstration dental template on said registration paste to align a tooth plane on said template with a desired horizontal facial plane such that said template appears horizontal relative to the horizontal facial plane;

setting said paste with said demonstration dental template in a set position; and removing said paste and demonstration dental template as an assembled unit from said natural teeth such that said paste has a negative surface corresponding in negative shape to buccal side of said natural teeth forming along said tooth plane and with said demonstration dental template maintaining the set position to record the position of the facial plane of the template relative to the tooth plane of said natural teeth.

\* \* \* \* \*